United States Patent [19] [11] 3,993,744
Cella et al. [45] Nov. 23, 1976

[54] LIVE HUMAN HAIR TREATMENT COMPOSITIONS CONTAINING PERFLUORINATED COMPOUNDS

[75] Inventors: John A. Cella, Plandone Mills, N.Y.; August Emil Fiebig, Jr., Chicago, Ill.

[73] Assignee: Alberto Culver Company, Melrose Park, Ill.

[22] Filed: May 31, 1974

[21] Appl. No.: 474,954

[52] U.S. Cl............................ 424/70; 424/DIG. 4; 424/359
[51] Int. Cl.² ......................................... A61K 7/06
[58] Field of Search............. 424/DIG. 4, 321, 70, 424/311, 313, 315, 224, 317, 321, 343, 359

[56] References Cited
UNITED STATES PATENTS

| | | | |
|---|---|---|---|
| 2,759,019 | 8/1956 | Brown et al. | 260/556 F |
| 2,803,656 | 8/1957 | Ahlbrecht et al. | 260/556 F |
| 2,809,990 | 10/1957 | Brown | 260/534 |
| 2,915,554 | 12/1959 | Ahlbrecht et al. | 260/556 F |
| 3,147,064 | 9/1964 | Brown et al. | 8/116.2 |
| 3,147,066 | 9/1964 | Brown et al. | 8/116.2 |
| 3,217,035 | 11/1965 | Lazerte et al. | 260/556 F |
| 3,245,817 | 4/1966 | Lovness | 106/279 |
| 3,708,537 | 1/1973 | Groves | 260/556 F |

Primary Examiner—Albert T. Meyers
Assistant Examiner—Vera C. Clarke
Attorney, Agent, or Firm—Wallenstein, Spangenberg, Hattis & Strampel

[57] ABSTRACT

Hair treatment compositions, of the type in which oil retardation is a desideratum, containing distinctly minor proportions of hydrophobic-lipophobic perfluorinated compounds.

20 Claims, No Drawings

LIVE HUMAN HAIR TREATMENT COMPOSITIONS CONTAINING PERFLUORINATED COMPOUNDS

Our invention is directed to improved hair treatment compositions for the treatment of hair on human heads.

It has long been known that the sebaceous glands in the human scalp substantially continuously secrete sebum which acts to keep the hair lubricated, smooth and shiny. It has also long been known that many people suffer from an over-production of sebum and, as a result, have oily hair. Oily hair readily picks up dust and other particulate matter from the environment which requires frequent hair shampooing, commonly as often as every day or every other day, in order to make the hair look clean and presentable.

The secretion products of the sebaceous glands, especially if produced in excess, frequently have an adverse effect on certain hair care products which are applied to the live human hair to impart desirable properties thereto in relation to texture, hold and general appearance. Among such hair treatment products, hair setting lotions, gels, hair conditioning products and hair sprays are most generally adversely affected by the sebum or natural oils secreted by the sebaceous glands. In this connection, it may be noted that such hair treatment products commonly contain resins or resinous ingredients, for instance, polyvinylpyrrolidone (PVP). The sebum or natural oils tend to plasticize the resins with the result that the desired properties of the resins are adversely affected, resulting in diminishing or loss of the holding power of the resins. The adverse effect of the sebum or natural oils secreted by the sebaceous glands is not, however, limited only to those hair treatment compositions which contain resins or resinous materials as ingredients thereof. Hair treatment compositions which impart to the hair such properties as body, sheen and a soft, silky touch, and which do not contain resins or resinous materials, are also commonly undesirably affected by reason of the spread of the sebaceous secretions along the hair shaft with the result that the hair becomes oily and sticky, depending upon the amount or extent of such secretions, measured, also, of course, as a function of time. In many instances it can be observed that resins or other materials deposited on hair speed up the spreading of the sebum along the hair shaft and, so, enhance the adverse effects of excess sebum.

We found that treatment of human hair in accordance with the practice of this invention greatly diminishes the speed of spreading sebum along the hair shaft and by doing so suppresses the adverse effects of excess sebum. Also when hair experiences no treatment after shampooing except treatment with the compositions of this invention, it will retard the flow of sebum which makes it possible to shampoo hair less often. Since frequent shampooing causes a certain damage to hair, the compositions of this invention diminish such damaging effects.

We have found that the incorporation into hair treatment compositions of distinctly minor proportions of hydrophobic-lipophobic perfluorinated chemical compounds highly effectively retards the excess flow of the sebum or sebaceous secretions and by doing so maintains the properties and utilities of the hair treatment compositions.

The aforementioned hydrophobic-lipophobic perfluorinated chemical compounds can be represented by the formula $$CF_3-(CF_2)_x-(CH_2)_y-Z$$

where Z is a water or oil solubilizing group of either organic or inorganic character, $x$ is an integer which is generally from 2 to 17, particularly from 7 to 11, and $y$ is an integer of 0 to 4, and said compounds may be anionic, cationic, nonionic or amphoteric, depending upon the nature of the grouping or groupings encompassed by Z. The Z groups may be or may comprise sulfonic, sulfate, phosphate, amide, alkyl-substituted amide, sulfonamido, carboxylic, quaternary ammonium, betainic and similar groups. The hydrophobic lipophobic perfluorinated compounds are per se known to the art and are identified by trademarks such as the FLUORADS (Minnesota Mining and Manufacturing Company) and ZONYL (E. I. du Pont de Nemours & Company). The water solubility and organic solvent solubility of the aforesaid compounds are, as is known, affected and can be controlled by varying the chain length of the perfluorinated hydrocarbon moiety and by the selection of Z as designated in the above-mentioned formula.

Illustrative samples of the hydrophobic-lipophobic perfluorinated compounds are the following:

$$CF_3-(CF_2)_7-SO_3H \quad (1)$$

$$CF_3-(CF_2)_7-SO_3M \quad (2)$$

$$CF_3-(CF_2)_7-SO_2-NH-CH_3 \quad (3)$$

$$CF_3-(CF_2)_9-SO_2-\underset{\underset{C_2H_5}{|}}{N}-CH_2-COOH \text{ (M)} \quad (4)$$

$$CF_3-(CF_2)_7-SO_2-\underset{\underset{CH_3}{|}}{N}-(C_2H_4O)_8H \quad (5)$$

$$CF_3-(CF_2)_9-SO_2-\underset{\underset{C_2H_5}{|}}{N}-C_2H_4-\overset{\overset{O}{\|}}{O}P(OH)_2 \text{ (M)} \quad (6)$$

$$CF_3-(CF_2)_{11}-SO_2-\underset{\underset{CH_3}{|}}{N}-CH_2CH_2OSO_3H \text{ (M)} \quad (7)$$

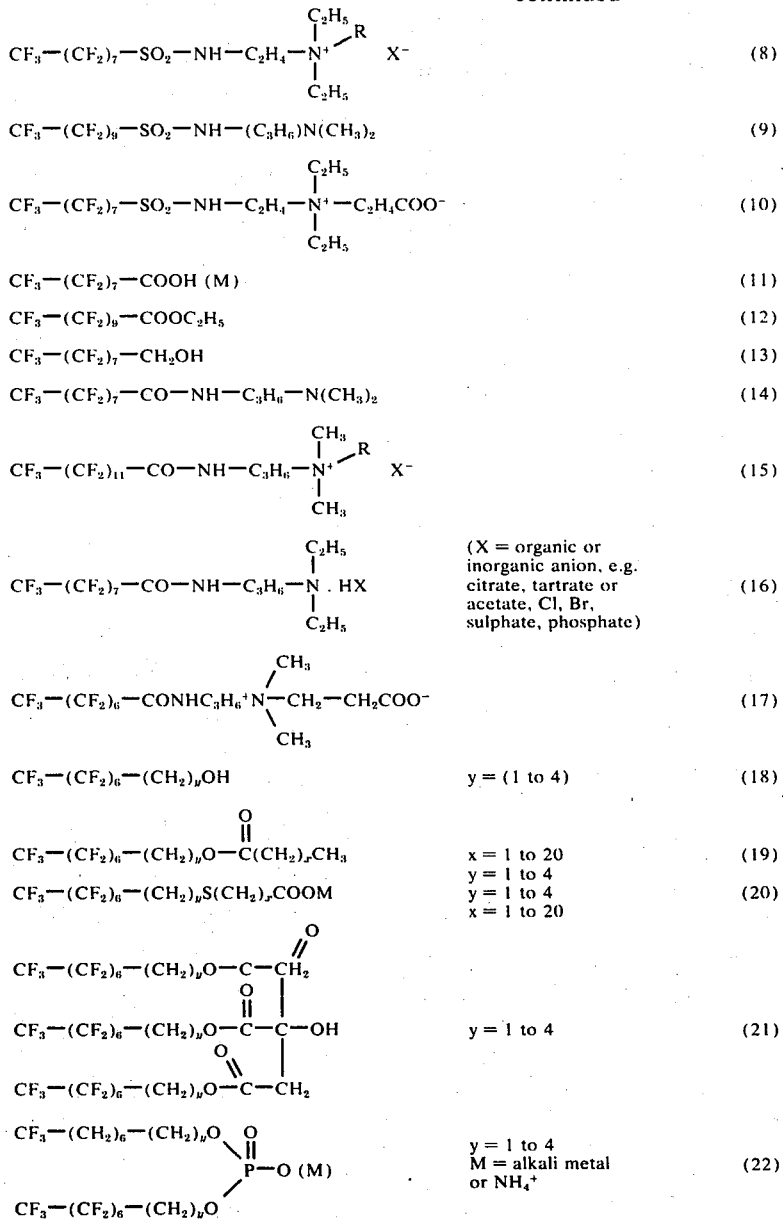

-continued

The aforesaid hydrophobic-lipophobic perfluorinated compounds are effective, in the hair treatment compositions of our present invention, in very low concentrations, as low as about 0.05%, by weight of the hair treatment compositions, to of the order of about 1% or 2% or slightly higher. As a general rule, proportions of the order of about 0.1% to 1% are generally adequate, with a good general average being about 0.1% to 0.5%. The lower limit is determined by the particular efficacy of the specific compounds in selected compositions, whereas the upper limit, not in excess of 10%, is usually governed by somewhat similar considerations except that, generally speaking, no more should be used than is necessary and, in addition, it is desirable not to exceed the solubility or ready dispersibility limits of the compound in the particular hair treatment composition involved, while maintaining homogeneity in said composition.

The hydrophobic-lipophobic perfluorinated compounds can be dissolved or dispersed in water or organic solvents, but especially in water-organic solvent mixtures the organic solvents being most desirably aliphatic alcohols, and being soluble in or at least partially miscible with water. The organic solvents include, by way of illustration, ethanol, isopropanol, Carbitol, acetone, and the like, or compatible mixtures, especially advantageous being ethanol. Where water-organic solvent mixtures are used, for instance, water-ethanol or water-isopropyl alcohol, the water content of the compositions or solutions utilized is generally in the range of about 15% to about 80%, and, better still, from about 20% to about 70% by weight of the compositions or solutions. The pH of the compositions or solutions may vary from 2.5 to 9. However, a pH between 3.5 and 7.5 is the range of choice. The hair treatment composition may also contain a combing aid as are represented by various cationic compounds, silicones, proteins and other supplemental ingredients for particular purposes including, for instance, desired perfume and color.

The following examples are illustrative but in no way limitative of the invention since many other hair treatment compositions can readily be made in light of the guiding principles and teachings contained herein. All percentages listed are by weight, unless otherwise specifically stated.

EXAMPLES

General Experimental Procedure

Approximately 15 cm. long hair swatches are tied on one end and shampooed to remove all alien residues. After drying, they are treated with the experimental composition. The samples are twisted into a rope and tied at the other end. All samples are dried at 30° C in an oven. Control samples are run in each case. Control samples and compositions of the invention samples were dipped into squalene containing an oil-soluble dye for 5 minutes, and the swatches plotted on paper to establish the oil travelling distance. Oil retardation is calculated according to formula. Unless otherwise specified, this procedure was followed in each example.

$$100 - \frac{B \cdot 100}{A} = \% \text{ retardation}$$

A = distance of oil travelled in untreated sample
B = distance of oil travelled in treated sample

EXAMPLE 1

| | |
|---|---|
| Ethanol | 30.00 |
| Water | 69.70 |
| Silicone* | 0.10 |
| Compound of Structure 11 | 0.10 |
| Perfume | 0.10 |
| | 100.00 |

*Polyoxyethylene Polymethyl Siloxane

In the preparation of the hair treatment composition of this Example 1, it is convenient to dissolve the compound of structure 11 in the water. Then the silicone and the perfume are dissolved in the ethanol and admixed with the water solution of the compound of structure 11.

Mixing procedures for other hair treatment compositions of the present invention, illustratively disclosed in the following Examples, will be apparent to those skilled in the art.

When a hair swatch was treated with this solution and compared to an untreated control sample, it exhibited an oil retardation of 85%.

EXAMPLE 2

| | |
|---|---|
| Isopropyl alcohol | 79.88 |
| Water | 20.00 |
| Compound of Structure 20 | 0.10 |
| Perfume | 0.02 |
| | 100.00 |
| 99% Retardation | |

EXAMPLE 3

| | |
|---|---|
| Ethanol | 30.00 |
| Water | 69.00 |
| Compound of Structure 22 | 1.00 |
| | 100.00 |
| 85% Retardation | |

EXAMPLE 4

| | |
|---|---|
| Ethanol | 30.00 |
| Water | 69.90 |
| Silicone* | 0.05 |
| Compound of Structure 15 | 0.05 |
| | 100.00 |
| 44% Retardation | |

*Polyoxyethylene Polymethyl Siloxane

EXAMPLE 5

| | |
|---|---|
| Ethanol | 30.00 |
| Water | 69.00 |
| Compound of Structure 19 | 1.00 |
| | 100.00 |
| 85% Retardation | |

EXAMPLE 6

| | |
|---|---|
| Ethanol | 30.00 |
| Water | 69.90 |
| Compound of Structure 11 | 0.10 |
| | 100.00 |
| 95% Retardation | |

EXAMPLE 7

| | |
|---|---|
| Isopropyl alcohol | 20.00 |
| Water | 78.75 |
| Cetyl trimethylammonium chloride | 0.10 |
| Compound of Structure 10 | 1.00 |
| Perfume | 0.15 |
| | 100.00 |
| 54% Retardation | |

EXAMPLE 8

| | |
|---|---|
| Ethanol | 30.00 |
| Water | 68.85 |
| Compound of Structure 16 | 1.00 |
| Perfume | 0.15 |
| | 100.00 |
| 44% Retardation | |

EXAMPLE 9

| | |
|---|---|
| Ethanol | 30.00 |
| Water | 68.85 |
| Compound of Structure 6 | 1.00 |
| Perfume | 0.15 |
| | 100.00 |
| 85% Retardation | |

We claim:
1. A composition for treating live human hair comprising water, an organic solvent or mixtures thereof which includes, as an ingredient thereof, a hydrophobic-lipophobic compound of anionic, cationic, nonionic or amphoteric character corresponding to the formula $$CF_3-(CF_2)_x-(CH_2)_y-Z$$

where Z is a member selected from the group consisting of a water-solubilizing groups and an oil-solubilizing group, $x$ is an integer from 2 to 17, and $y$ is an integer from 0 to 4, said compound being present in proportions, based on the weight of the composition, in the range of about 0.05% to not in substantial excess of the solubility or ready dispersibility of said compound in the composition and not in excess of 10%, said composition also containing, as an additional ingredient, a combing aid selected from the group consisting of cationic compounds, silicones and proteins.

2. The composition of claim 1, in which the proportions of said compound are in the range of about 0.1% to about 1%.

3. The composition of claim 1, in which said compound is in solution in a mixture of water and a water-soluble aliphatic alcohol in which the water content of said solution is in the range of about 15% to about 80% by weight of said composition.

4. The composition of claim 3, in which the water content is in the range of about 20% to about 70% by weight of said composition.

5. The composition of claim 3, in which the alcohol is a member selected from the group consisting of ethanol and isopropyl alcohol.

6. The composition of claim 4, in which the alcohol is a member selected from the group consisting of ethanol and isopropyl alcohol.

7. The composition of claim 1, in which, in the hydrophobic-lipophobic compound, $x$ is 7 to 11.

8. The composition of claim 7, in which Z is a member selected from the group consisting of sulfonic, sulfate, carboxyl, phosphate and quaternary ammonium groups.

9. The composition of claim 7, in which the hydrophobic-lipophobic compound is anionic in character.

10. The composition of claim 7, in which the hydrophobic-lipophobic compound is cationic in character.

11. A method of retarding the flow of sebum along the hair shafts of hair on the human head which comprises contacting said hair with a solution containing from about 0.05% to 10% by weight of a hydrophobic-lipophobic compound of anionic, cationic, nonionic or amphoteric character corresponding to the formula $$CF_3-(CF_2)_x-(CH_2)_y-Z$$

where Z is a member selected from the group consisting of a water-solubilizing groups and an oil-solubilizing group, $x$ is an integer from 2 to 17, and $y$ is an integer from 0 to 4.

12. The method of claim 11, in which the hydrophobic-lipophobic compound is present in proportions in the range of about 0.05% to 0.2% by weight of said solution.

13. The method of claim 11, in which the solution of said hydrophobic-lipophobic compound is a solution in a mixture of water and a water-soluble aliphatic alcohol in which the water content of said solution is in the range of about 15% to about 80% by weight of said solution.

14. The method of claim 13, in which the water content is in the range of about 20% to about 70% by weight of said solution.

15. The method of claim 13, in which the alcohol is a member selected from the group consisting of ethanol and isopropyl alcohol.

16. The method of claim 14, in which the alcohol is a member selected from the group consisting of ethanol and isopropyl alcohol.

17. The method of claim 11, in which, in the hydrophobic-lipophobic compound, $x$ is 7 to 11.

18. The method of claim 17, in which Z is a member selected from the class consisting of sulfonic, sulfate, carboxyl, phosphate and quaternary ammonium groups.

19. The method of claim 17, in which the hydrophobic-lipophobic compound is anionic in character.

20. The method of claim 17, in which the hydrophobic-lipophobic compound is cationic in character.

* * * * *